United States Patent [19]
Safi

[11] Patent Number: 5,681,470
[45] Date of Patent: Oct. 28, 1997

[54] METHOD OF EXTRACTING LIGHT VOLATILE SOLVENTS FROM A GASEOUS EFFLUENT BY WET-SCRUBBING A GASEOUS EFFLUENT AND BIOMETHANATION OF THE SOLVENT-RICH LIQUID

[75] Inventor: Bechara Safi, Ville-St-Laurent, Canada

[73] Assignee: Societe de Recherche SNC Inc., Canada

[21] Appl. No.: 541,206

[22] Filed: Oct. 12, 1995

[51] Int. Cl.$^6$ .................................................. C02F 3/28
[52] U.S. Cl. .................... 210/603; 210/610; 210/631; 210/150; 210/188; 210/195.1; 210/916; 55/228; 95/187; 435/266
[58] Field of Search ........................... 210/603, 615, 210/617, 631, 150, 157, 188, 916, 195.1, 202, 258, 259, 610, 611; 435/266; 55/228; 95/187

[56] References Cited

U.S. PATENT DOCUMENTS

| | | | |
|---|---|---|---|
| 4,351,729 | 9/1982 | Witt | 210/617 |
| 4,654,308 | 3/1987 | Safi | 435/310 |
| 4,662,900 | 5/1987 | Ottengraf | 210/615 |
| 4,723,968 | 2/1988 | Schippert et al. | 210/151 |
| 4,781,732 | 11/1988 | Wondrasch et al. | 435/266 |
| 4,781,836 | 11/1988 | Thiele et al. | 210/603 |
| 4,869,819 | 9/1989 | Thiele et al. | 210/195.1 |
| 4,894,162 | 1/1990 | Cournoyer et al. | 210/603 |
| 4,931,401 | 6/1990 | Safi | 210/150 |
| 4,936,996 | 6/1990 | Messing | 210/603 |
| 4,959,084 | 9/1990 | Wolverton et al. | 210/615 |
| 5,077,025 | 12/1991 | Glass | 435/266 |
| 5,080,793 | 1/1992 | Urlings | 210/603 |
| 5,143,835 | 9/1992 | Nakatsugawa et al. | 210/603 |
| 5,246,584 | 9/1993 | Donaldson et al. | 210/603 |
| 5,316,940 | 5/1994 | Georgiou et al. | 435/262 |

FOREIGN PATENT DOCUMENTS

| | | |
|---|---|---|
| 282750 | 9/1988 | European Pat. Off. . |
| 2643211 | 4/1978 | Germany . |
| 57-180421 | 11/1982 | Japan . |

Primary Examiner—Christopher Upton
Attorney, Agent, or Firm—Andrus, Sceales, Starke & Sawall

[57] ABSTRACT

An improved method and apparatus for treating a gaseous medium polluted with volatile organic solvents to produce a purified gaseous medium and a separate methane-rich and combustible gas. The method involves wet-scrubbing the gaseous medium with a liquid stream in a countercurrent wet scrubber to produce a purified gaseous medium and a separate liquid stream loaded with the volatile organic solvents; channelling the liquid stream loaded with the volatile organic solvents to an anaerobic bioreactor consisting of a sealed vessel containing a biomass having methanogenic bacteria adapted to transform the volatile organic solvents into a methane-rich and combustible gas and a separate liquid stream output substantially free of the volatile organic solvents; recovering the methanerich and combustible gas by collecting the gas from the anaerobic bioreactor.

14 Claims, 2 Drawing Sheets

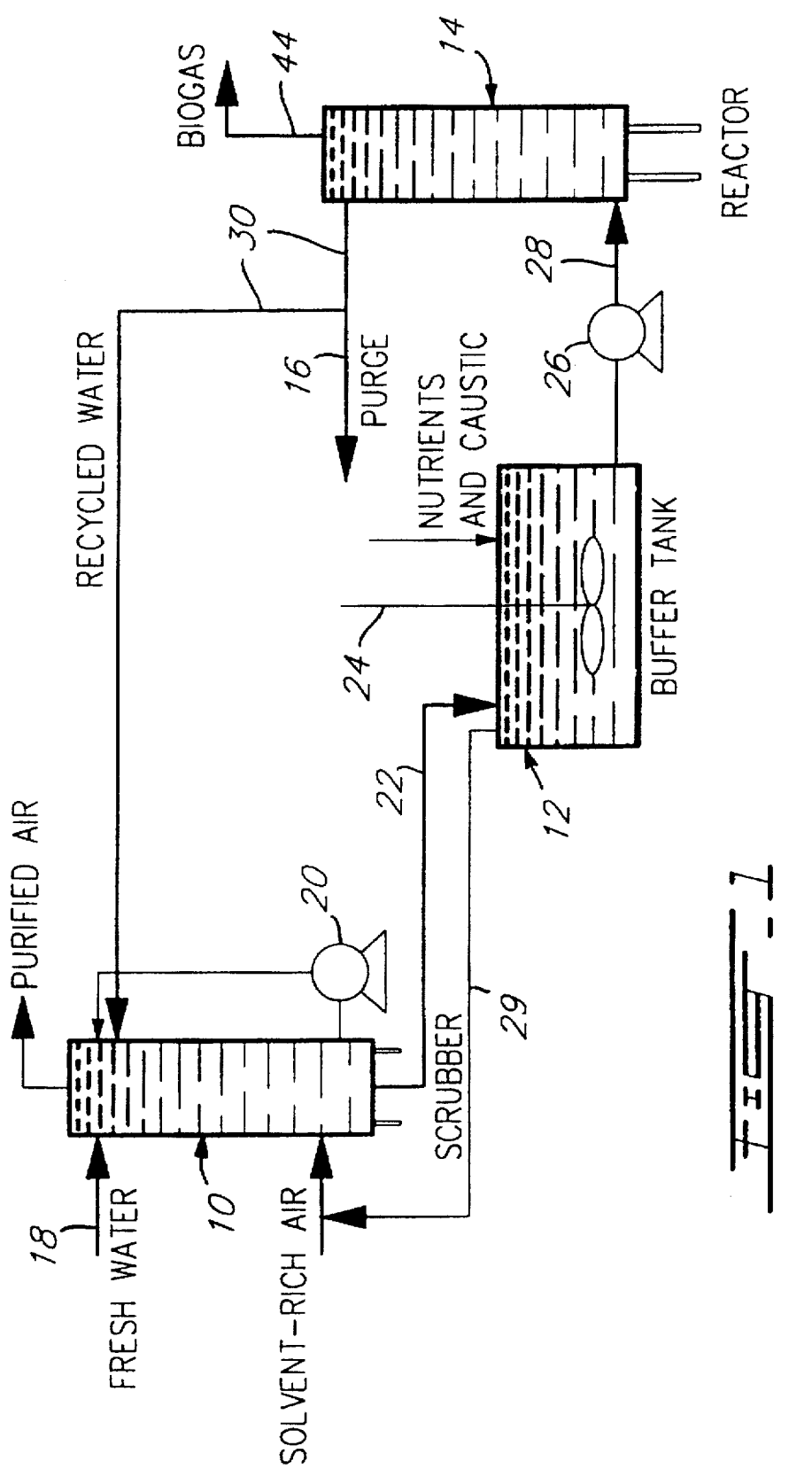

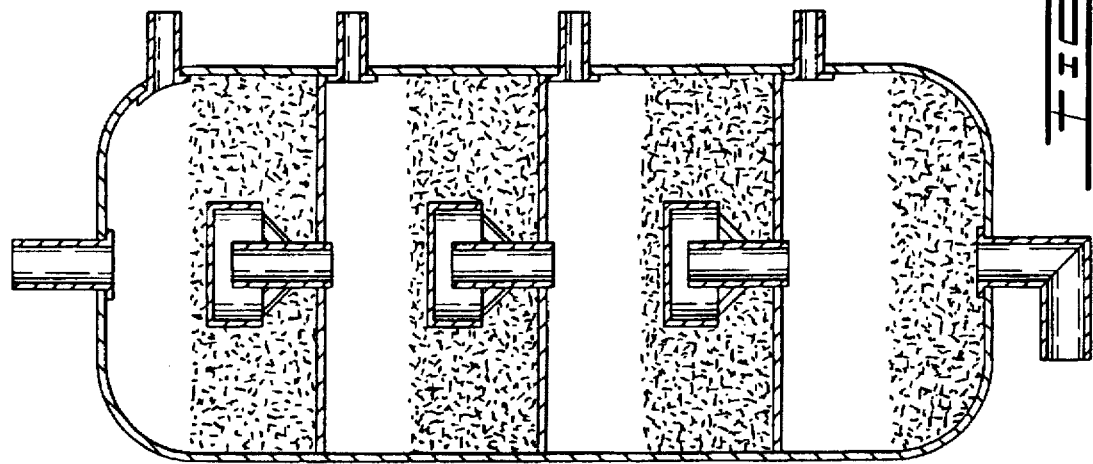
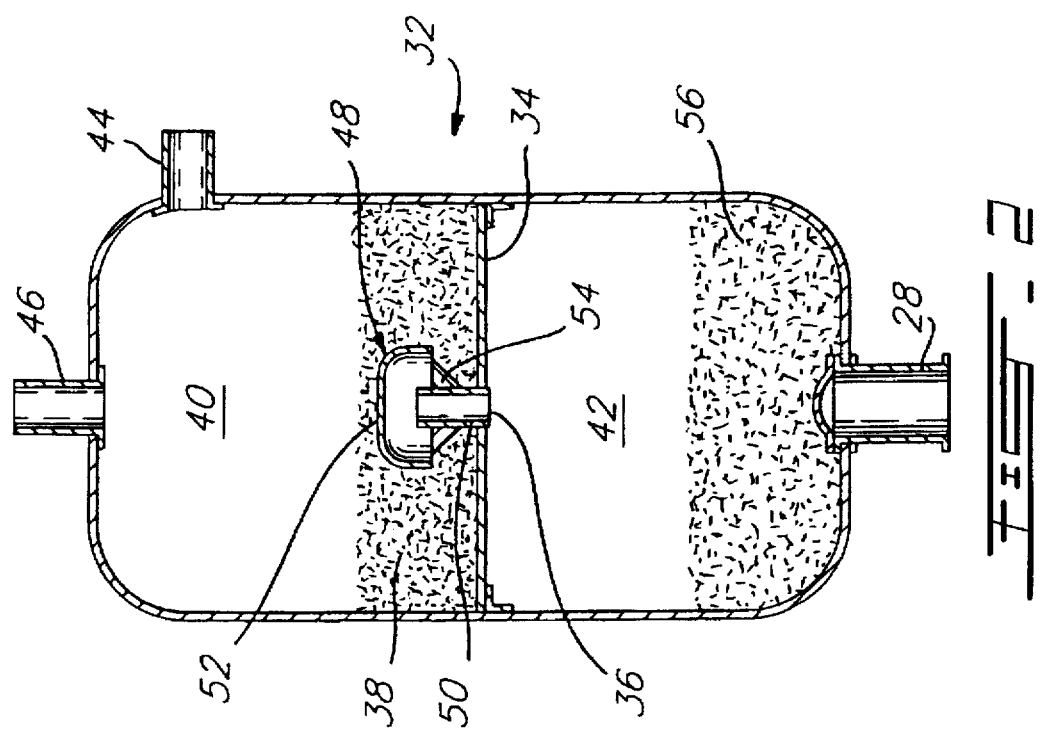

METHOD OF EXTRACTING LIGHT VOLATILE SOLVENTS FROM A GASEOUS EFFLUENT BY WET-SCRUBBING A GASEOUS EFFLUENT AND BIOMETHANATION OF THE SOLVENT-RICH LIQUID

BACKGROUND OF THE INVENTION

1. Field of the Invention

The present invention relates to a method for the treatment of gaseous effluents containing volatile organic compounds (VOCs). More specifically, the method involves loading the VOCs in an aqueous liquid stream by wet-scrubbing and subjecting the VOC-loaded liquid stream to an anaerobic biomethanation step which provides a methane-rich and combustible gaseous output and a purified liquid stream suitable for recycling. The present invention also relates to an apparatus for carrying-out the method of the invention.

2. Description of the Prior Art

Volatile organic compounds (VOCs) are commonly found as solvents and quick-drying agents in printing inks. Such inks are commonly used by the flexographic printing industry. During flexography printing, liquid inks are deposited on plastic and aluminum films and it is during the drying of those inks that VOCs are vaporized as by-products into ambient air. VOCs represent a significant source of air pollution which may lead to serious health risks for those exposed to the pollutants. Reported VOC-related health problems include respiratory ailments and even lung cancer, mental disorders as well as a variety of skin disorders. In the flexographic printing industry, by-product VOCs consist mainly of mixtures of alcohols such as ethanol, methanol, n-propanol and iso-propanol and may also comprise ethyl acetate. When released into the atmosphere, VOCs are sometimes degraded by ultraviolet rays and transformed into ozone, a toxic component or urban smog. VOCs are also generated by a variety of other industrial processes.

Several different technologies have been used to control VOC emissions. The solutions currently used in North America consist of three main strategies: recovery of the solvents by condensation or adsorption on activated carbon; destruction by thermal or catalytic incineration; or replacement of the VOC solvent-based inks with water-based inks. These techniques have met with some success but have inherent high operating costs and in the case of water-based inks have the important drawback of requiring longer ink drying times.

It has also been suggested to treat gaseous VOCs by biofiltration through a fixed bed containing bacteriological or mycological cultures on mixtures of mosses, branches and/or compost. The terms "biofiltration" or "bioreactor" used herein refer to a process or equipment in which chemical transformations are carried out by living microorganisms. However, in the case of gas phase biofiltration, design and operation parameters are still unmastered because of the inherent instability and fragility of the biofiltration beds.

Liquid phase bioreactors are also known for the treatment of liquid effluents containing organic matter, such as in the pulp and paper industry or the cheese making industry. The design of such bioreactors was stimulated by pollution regulations imposed by governmental authorities. Examples of such bioreactors can be found to be described in U.S. Pat. 4,654,308 and 4,931,401 both to Safi et al., the specifications of which are incorporated herein by reference and in U.S. Pats. 4,869,819 to Theile et al., 4,351,729 to Witt, and 4,936,996 to Messing. Furthermore, considerable effort has been put into developing new strains of microorganisms capable of degrading various organic compounds including highly toxic chlorinated hydrocarbons. Recent efforts are exemplified in U.S. Pats. 5,316,940, to Georgiou et al. and 5,143,835 to Nakatsugawa et al.

With most bioreactors, it is commercially and environmentally desirable to degrade the organic compounds into methane such degradation being commonly referred to as "methanogenesis". This produces a methane-rich and combustible gaseous effluent which can cleanly burn to provide process heat or otherwise used to improve process economics.

Hence, there is a need for a commercially and technically efficient method and apparatus for treating gaseous effluents containing VOCs to obtain a purified gaseous effluent and to concurrently generate methane-rich combustible gas by biological conversion. It is an object of the present invention to meet this need.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

SUMMARY OF THE INVENTION

The foregoing objects and additional objects are achieved by the present invention which in one main aspect provides a method for the biodegradation treatment of a gaseous medium polluted with volatile organic solvents to produce a purified gaseous medium and a separate methane-rich and combustible gas, the novel and inventive method comprising the steps of:

(a) wet-scrubbing the gaseous medium with a liquid stream in a countercurrent wet scrubber to produce a purified gaseous medium and a separate liquid stream loaded with the volatile organic solvents;

(b) flowing said liquid stream loaded with the volatile organic solvents to an anaerobic bioreactors consisting of a sealed vessel containing a biomass having methanogenic bacteria adapted to transform the volatile organic solvents into a methane-rich and combustible gas and a separate liquid stream output substantially free of the volatile organic solvents;

(c) recovering the methane-rich and combustible gas by collecting said gas from said anaerobic bioreactor.

In a related aspect, the present invention provides a novel and inventive apparatus for accomplishing the method of the present invention. Hence, there is provided an apparatus for the biodegradation treatment of a gaseous medium polluted with volatile organic solvents and the production of a purified gaseous medium and a separate methane-rich and combustible gas, the apparatus comprising:

(a) a countercurrent wet scrubber unit for counter currently receiving the polluted gaseous medium and a liquid stream so as to produce a purified gaseous medium and a separate liquid stream loaded with the volatile organic solvents, the wet scrubber unit consisting of at least one closed vessel;

(b) an anaerobic bioreactor for receiving the liquid stream loaded with the volatile organic solvents, the anaerobic bioreactor consisting of a sealed vessel containing a biomass having methanogenic bacteria adapted to transform the volatile organic solvents into the methane-rich and combustible gas and a separate liquid stream output substantially free of the volatile organic solvents, the bioreactor being provided with an output stream for the liquid stream output and an output valve for the methane-rich and combustible gas; and (c) fluid transportation lines connecting the wet scrubber and the anaerobic bioreactor for flowing said liquid stream loaded with said volatile organic compounds from the wet scrubber to the anaerobic bioreactor.

BRIEF DESCRIPTION OF THE DRAWINGS

FIG. 1 is a schematic view of the preferred apparatus for a continuous process in accordance with the method of the present invention.

FIG. 2 is a schematic elevational and sectional view of a bioreactor as a component of the apparatus of the present invention.

FIG. 3 is a schematic elevational and sectional view of an optional embodiment of the bioreactor of FIG. 2.

DETAILED DESCRIPTION OF THE INVENTION

Process description

Referring to FIG. 1, the process apparatus mainly comprises a water scrubber 10, a buffer tank 12, and a multi plate anaerobic bioreactor 14. The process apparatus is characteristically operated as a closed loop system. However, to avoid accumulation of mineral residues, a purge line 16 is provided. Periodic and minor purges are compensated by the addition of fresh water by line 18.

Scrubber

Air emissions loaded with volatile organic compounds (VOCs) are channeled to a conventional scrubber unit 10 wherein the VOCs are transferred from the air (gas phase) by counter currently contacting a water stream (liquid phase). The clean air can be safely discharged to the atmosphere after removal of the VOCs.

It is of course to be understood that the solvents must be water soluble for the phase transfer to take place in a water scrubber. However, to facilitate the entry of the VOCs into solution, it is contemplated that solubility enhancers may be used. For example, surfactants can be added to the water in the scrubber to enhance the solubility of certain organic compounds. It is also conceivable that non-aqueous liquid solutions be used. However, the non-aqueous solutions would have to be compatible with the biomethanation microorganisms found in the bioreactor 14.

In a preferred embodiment, the scrubber 10 is composed of three vertical cylinders 10, 10'(not shown) and 10"(not shown), serially disposed. Other types of scrubbers and scrubber arrangements can be used but this type has been shown to give the best results to date. Packing is preferably not used, in order to avoid clogging caused by biomass particles recycled from the bioreactor 14. If required, additional scrubbing cylinder sections can be added, to enhance the solvent removal efficiency. In operation, the air enters the bottom of the scrubber 10 and exits at the top. It then enters a second scrubber 10'(not shown) at the top and exits at the bottom for subsequent entry into the bottom of the last cylinder 10"(not shown) from which it exits at the top. Meanwhile follows a countercurrent flow starting at the top of the third cylinder 10"(not shown). The water level is maintained by a liquid level controller(not shown) connected to scrubber 10.

Water loss due to evaporation or purge is automatically compensated by fresh water addition through fresh water line 18. A centrifuge pump 20 is used to transport the water in each section of the scrubber. Sprinklers (not shown), inside scrubbers 10, 10' and 10" are used to spray the water thereby ensuring good contact between the water and the VOC containing air. It is noted that the sprinkler nozzles must be large enough to avoid clogging with the biomass particles that may be circulating in the apparatus of the present invention but also small enough to pulverize the water into small droplets into the VOC containing air. The number and placement of sprinklers will be readily determined by one knowledgeable in the design and operation of wet scrubbers. The main goal is of course to maximize the gas to liquid contact to promote solubilization of the VOCs in the water. In a preferred embodiment, the sprinklers are installed at spaced intervals to spray vertically and counter currently to the air flow.

Buffer tank

An agitated and closed buffer tank 12 is connected to said fluid transportation lines between said wet scrubber 10 and said anaerobic bioreactor 14 to allow a blending of said liquid stream loaded with the volatile organic solvents to provide a blended output stream thereby avoiding sharp peaks or drops in concentration of volatile organic solvents flowed to said anaerobic bioreactor.

A tank liquid level controller (not shown) is provided for controlling the amount of liquid in tank 12 and for controlling the flow out of tank 12 and to the anaerobic bioreactor 14. In a preferred embodiment and at steady state, the liquid volume of the buffer tank 12 is the same as liquid volume of bioreactor 14.

Meanwhile, tank 12 is also provided with a temperature controller (not shown) for measuring and controlling the temperature of said liquid stream and a pH controller (not shown) for measuring and controlling the pH of said liquid stream. Hence, the aqueous stream loaded with solubilized VOCs exiting scrubber unit 10 is directed to the buffer tank 12 through line 22. In a preferred embodiment, the water enters the buffer tank 12 by gravity.

Although significant levels of oxygen are solubilized in the water during the scrubbing process, they are quickly depleted by facultative bacteria present in tank 12.

Various nutrients and trace heavy metals can be added to tank 12 to optimize the growth of the acidogenic and acetogenic bacteria. These bacteria partially convert the solubilized VOCs to organic acids including acetic, proprionic and butyric acids. Typically, 60% of the total VOCs are converted to organic acids. Characteristically, nutrients are added as a concentrate. The amount of nutrients to be added to tank 12 is based on the organic load entering buffer tank 12 and the amount of purge from the system (i.e. the nutrients which are purged must be replaced). Among the various possible nutrients, dried yeast may be added to provide vitamins to the anaerobic bacteria in bioreactor 14.

The temperature in buffer tank 12 is monitored and maintained by any suitable, commercially available controller (not shown). In a preferred embodiment, the controller is of the type having a thermostat which controls a source of hot water which is regulated in temperature and flow rate to enter a heat exchanger(not shown) which is in the form of a stainless steel spiral. It has been observed that generally, the optimal temperature of buffer tank 12 is between 35 and 40° C., however, a temperature of 30° C. has been found to be sufficient to provide proper operation of bioreactor 14.

The pH level in buffer tank 12 is maintained by any suitable commercially available pH controller. In a preferred embodiment, a pH controller is provided with a dosage pump adapted to add the appropriate amounts of acid or base to maintain the pH at a given level in tank 12. Although any acid can be used, acetic acid has been found to give good results since it will not accumulate in the closed system. Caustic soda (50% NaOH) or other suitable base is added when the pH is too low. Calcium hydroxide can also be added daily to maintain proper alkalinity. Other compounds such as sodium bicarbonate can be used for the same purpose. It has been observed that the optimal pH is in the range of 5.5 to 6.5, with the preferred pH being 6.0. A mechanical agitator 24 is used to maintain continuous mixing and a mono pump 26 is used to feed the aqueous solution through line 28 connecting the bottom of buffer tank 12 and bioreactor 14.

It is apparent that a small portion of the VOCs in the aqueous solution of buffer tank 12 tend to evaporate back into the gaseous phase above the liquid level in tank 12. To recuperate these VOCs, the solvents are firstly captured due to the enclosed nature of the tank 12 and channeled via return tubing 29 to scrubber unit 10 which operates under a negative pressure. The carbon dioxide generated microbially from buffer tank 12 is also channeled back to scrubber unit 10 via the same return tubing.

Anaerobic treatment

The aqueous solution from buffer tank 12 is pumped by mono pump 26 through line 28 and into bioreactor 14 wherein it undergoes methanogenesis anaerobic treatment by being contacted with a biomass of methanogenic microorganisms. Hence, the VOCs and their organic acids intermediates are transformed into combustible biogas (methane and carbon dioxide) by the methanogenic bacteria residing in bioreactor 14. The biogas bubbles out of the aqueous stream which is thereby purified and suitable for reuse in scrubber unit 10. Consequently, the effluent aqueous stream exiting the bioreactor 14 through line 30 is recycled to the scrubber unit 10. As previously mentioned, a purge is available on line 30 to allow the removal from the effluent of bioreactor 14 to avoid accumulation of inert substances in the system such as the products of bacterial lysis, unused yeast extracts, etc. A minor purge allows to minimize the use of fresh water and nutrient addition. The purge is usually in the range of 5 to 30% vol of the entire aqueous flow through the system, with 10% vol being preferred. In most circumstances, the purge will contain innocuous traces of VOCs and can be safely discharged without further treatment.

Although any suitable anaerobic bioreactor can be used the best results have been obtained using a multi plate bioreactor substantially as described in U.S. Pat. No. 4,931, 401, the disclosure of which is incorporated herein by reference. A preferred embodiment of the bioreactor 14 will now be briefly described.

Referring to FIG. 2, there is shown schematically a bioreactor 14 having an inlet line 28 allowing the aqueous stream to be treated. The bioreactor comprises a container 32 having an intermediate horizontal plate 34 having a central aperture 36. A bed 38 of microorganisms is supported on plate 34.

Plate 34 divides the container 32 in an upper compartment 40 and a lower compartment 42. In upper compartment 40, a first outlet 44 is provided for discharging treated aqueous stream while a second outlet 46 is used for discharging the volatile biogas which is formed by the reaction of the aqueous stream with the microorganisms.

The microorganisms preferably consist of granular methanogenic bacteria capable of converting VOCs and their volatile organic acids to biogas containing combustible methane. The granular nature of the bacteria enables the bacteria to remain in the bioreactor 14. This consortium of bacteria having been acclimatized to the solvent substrates. The levels of biomass in each section are monitored to ensure the stability of the system.

A mushroom shaped blockage element, generally identified as 48, is provided over aperture 36 and comprises a tubular portion 50 extending upwardly from aperture 36 and a cap portion 52 extending over the tubular portion 50 and supported thereon by means of three arms 54.

The container 32 will also preferably comprise a second bed of microorganisms resting on the bottom 56 of container 32.

In operation, the bioreactor 14 receives an aqueous stream to be treated via inlet line 28 and reacts with the microorganisms resting on the bottom 56 of container 32. Continuous flow of pumped liquid in container 32 causes the aqueous stream and the biogas to pass through aperture 36 to the upper compartment 40 where the aqueous stream again reacts with the second bed 38 of microorganisms.

The blockage element 48 acts as a "check valve" to prevent backflow of aqueous stream and microorganisms from the upper compartment 40 to the lower compartment 42. The space situated under cap 52 fills with biogas which eventually bubbles to exhaust line 56. Meanwhile, the purified aqueous stream is recycled to the scrubber unit 10 through line 30.

In a preferred embodiment, more than one biogas exhaust line is provided. The biogas exhaust line are provided with a level indicator and a valve for releasing the biogas. The gas flow rate is monitored by a gas meter and the gas has been shown to be composed of at least 75% methane as shown by gas chromatography, the remainder being carbon dioxide. No traces of solvents have been found indicating conversion to methane without solvent evaporation. The produced gas could be subsequently used to replace natural gas in the plant.

Also in a preferred embodiment, the pH in the bioreactor 14 is maintained between 6.5 and 7.5, with 7.0 being preferred.

It will be understood by those skilled in the art that many bioreactor design changes could be made without departing from the present invention. For example, as shown in FIG. 3, a multilevel bioreactor 58 could readily be used to improve conversion efficiencies at higher VOC loading rates.

The clean aqueous effluent leaving the reactor is approximately at 35° C. As mentioned previously, a small purge is removed before the bulk of the clean aqueous effluent is recycled back to the scrubber unit 10. The system thus operates as a closed loop.

The invention will now be further described by way of example provided for illustrative purposes.

EXAMPLE 1

A pilot system including a water scrubber, 900 L buffer tank and 900 L bioreactor (as described herein) were used to treat a portion of the air emissions from a flexographic plant, the emissions containing VOCs. The VOCs are generated during the drying of the inks used for printing aluminum and plastics films. The air removed from the presses thus contains high concentrations of VOCs. A portion of this air flow was diverted to the scrubber (253 $m^3$/h). The composition of VOCs treated was methanol (4%), ethanol (42%), iso-propanol (2%) and n-propanol (52%). The water flow through the system was 75 L/h. A liquid purge of 10% from the system was used. The operational conditions and bioreactor performance are shown in the Table II. Analysis by the chemical oxygen demand (COD) was used as a guide to reactor performance. The composition of the biogas produced from the bioreactor was 79.2% methane, 17.6% carbon dioxide and 3.2% water with no solvents detected. The results for the individual solvents for the scrubber and bioreactor performance are shown in Tables III and IV. The solvent concentrations in the air and water were monitored by a gas chromatograph. The overall performance of the system is indicated in Table V by a mass balance on the overall process. The inlet air emissions are the source of solvents for treatment whereas the air outlet and the water purge from the reactor make up the two sources of untreated solvent discharge.

TABLE I

AVERAGE DAILY OPERATIONAL CONDITIONS AND RESULTS

| | | |
|---|---|---|
| Bioreactor retention time (h) | | 12 |
| Bioreactor Feed Rate (L/day) | | 1800 |
| Purge from the reactor (% of feed rate) | | 10 |
| Gas flow produced by the bioreactor (L/j) | | 3046 |
| Neutralizing agents | Ca(OH)$_2$(powder)(g/day) | 248.0 |
| | NaOH 50% (L/day) | 50.0 |
| | Acetic acid 99% (L/day) | 450.0 |
| Additives | Heavy metals and nutrients as per Table II | |
| | Dried yeast (g/day) | 22.0 |
| Feed to reactor | Temperature (°C.) | 38.3 |
| | pH | 6.0 |
| | total COD (mg/L) | 5469.0 |
| | soluble COD (mg/L) | 4707.0 |
| Exit from reactor | Temperature (°C.) | 35.5 |
| | pH | 6.8 |
| | total COD (mg/L) | 1206.0 |
| | soluble COD (mg/L) | 572.0 |
| COD yield | Total | 78.0 |
| | Soluble | 88.0 |
| Gas factor (m$^3$/kg COD converted) | | 0.43 |
| Organic load (kg COD/m$^3$-day) | | 9.4 |

TABLE II

NUTRIENTS ADDED TO THE BUFFER TANK

| Element | Nutrient | Quantity added (g/kg DCO) |
|---|---|---|
| N | (NH$_2$)$_2$CO | 5.65 |
| P | (NH$_4$)$_2$HPO$_4$ | 1.50 |

| Metals | Salts | (mg/kg DCO) |
|---|---|---|
| Al | Al$_2$(SO$_4$)$_3$ | 1.9 |
| Ca | CaCl$_2$—6H$_2$O | 693.8 |
| Co | CoCl$_2$ | 4.02 |
| Cu | CuCl$_2$ | 0.6 |
| Fe | FeCl$_3$—6H$_2$O | 482.1 |
| Mg | MgSO$_4$—7H$_2$O | 2563.5 |
| Mn | MnSO$_4$—H$_2$O | 3.1 |
| Mo | (NH$_4$)$_6$Mo$_7$O$_{24}$-4H$_2$O | 0.2 |
| Ni | NiCl$_2$—6H$_2$O | 2.0 |
| Zn | ZnCl$_2$ | 6.3 |

TABLE III

AVERAGE SOLVENT CONCENTRATION IN THE FEED AND EFFLUENT OF THE SCRUBBER AND REMOVAL EFFICIENCIES

| SOLVENTS | FEED (MG/M$^3$) | EFFLUENT (MG/M$^3$) | REMOVAL RATE (% WEIGHT) |
|---|---|---|---|
| Methanol | 57.0 | 0.0 | 100.0 |
| Ethanol | 597.0 | 34.0 | 94.0 |
| Iso-Propanol | 34.0 | 4.0 | 88.0 |
| Propanol | 746.0 | 69.0 | 91.0 |
| Total: | 1,434.0 | 107.0 | 92.5 |

TABLE IV

AVERAGE SOLVENT CONCENTRATION IN THE INFLUENT AND EFFLUENT OF THE REACTOR AND REMOVAL EFFICIENCIES

| SOLVENTS | FEED (MG/M$^3$) | EFFLUENT (MG/M$^3$) | REMOVAL EFFICIENCY (% WEIGHT) |
|---|---|---|---|
| Methanol | 44.0 | 0.0 | 100.0 |
| Ethanol | 400.0 | 7.0 | 98.0 |
| Iso-Propanol | 44.0 | 4.0 | 97.0 |
| Propanol | 303.0 | 3.0 | 99.0 |
| Total: | 791.0 | 14.0 | 99.0 |

TABLE V

OVERALL SOLVENT REMOVAL EFFICIENCIES OF THE COMPLETE AIR TREATMENT PROCESS

| SOLVENTS | AIR INLET (G/H) | AIR + LIQUID EFFLUENTS (G/H) | REMOVAL EFFICIENCY (% WEIGHT) |
|---|---|---|---|
| Methanol | 14.4 | 0.0 | 100.0 |
| Ethanol | 151.0 | 9.1 | 94.0 |
| Iso-Propanol | 8.6 | 1.3 | 85.0 |
| Propanol | 188.7 | 17.7 | 90.6 |
| Total: | 362.7 | 28.1 | 92.3 |

The air flow rate in the scrubber was 253 m$^3$/h
The liquid flow in the system was 75 L/h.

Although the invention has been described above with respect with one specific form, it will be evident to a person skilled in the art that it may be modified and refined in various ways. It is therefore wished to have it understood that the present invention should not be limited in scope, except by the terms of the following claims.

The embodiments of the invention in which an exclusive property or privilege is claimed are defined as follows:

1. A method for the biodegradation treatment of a gaseous medium polluted with volatile organic solvents to produce a purified gaseous medium and a separate methane-rich and combustible gas, said method comprising the steps of:

(a) wet-scrubbing said gaseous medium with a liquid stream in a countercurrent wet scrubber to produce a purified gaseous medium and a separate liquid stream loaded with said volatile organic solvents;

(b) flowing said liquid stream loaded with the volatile organic solvents to an anaerobic bioreactor consisting of a sealed vessel containing a biomass having methanogenic bacteria adapted to transform the volatile organic solvents into said methane-rich and combustible gas and a separate liquid stream output substantially free of the volatile organic solvents;

(c) recovering said methane-rich and combustible gas by collecting said gas from said anaerobic bioreactor.

2. The method of claim 1, wherein in step (a), said liquid stream is an aqueous stream.

3. The method of claim 1, wherein said volatile organic solvents are water-soluble.

4. The method of claim 1, wherein between step (a) and step (b) there are the additional steps of: flowing said liquid stream loaded with said volatile organic solvent into a buffer tank, quickly deleting oxygen contained in said liquid stream, adding nutrients and adjusting the pH of the resulting liquid solution prior to flowing said liquid solution to said bioreactor in accordance with step (b) so as to optimize the steady-state operation of said bioreactor.

5. The method of claim 1, wherein said method is conducted continuously in a closed loop system wherein said liquid stream output from said bioreactor is continuously recycled to said wet-scrubber, said closed loop system also being provided with a make-up fresh liquid stream to said wet-scrubber and a purge stream so as to prevent accumulation of substances in said closed loop system.

6. The method of claim 1, wherein in step (a), surfactants are added to said wet scrubber so as to increase the solubility of said volatile organic compounds into said liquid stream.

7. An apparatus for the biodegradation treatment of a gaseous medium polluted with volatile organic solvents and the production of a purified gaseous medium and a separate methane-rich and combustible gas, said apparatus comprising:

(a) a countercurrent wet scrubber unit for counter currently receiving said polluted gaseous medium and a liquid stream so as to produce a purified gaseous medium and a separate liquid stream loaded with said volatile organic solvents, said wet scrubber unit consisting of a at least one closed vessel;

(b) an anaerobic bioreactor for receiving said liquid stream loaded with the volatile organic solvents, said anaerobic bioreactor consisting of a sealed vessel containing a biomass having methanogenic bacteria adapted to transform the volatile organic solvents into said methane-rich and combustible gas and a separate liquid stream output substantially free of the volatile organic solvents, said bioreactor being provided with an output stream for said liquid stream output and an output valve for said methane-rich and combustible gas; and (c) fluid transportation lines connecting said wet scrubber and said anaerobic bioreactor for flowing said liquid stream loaded with said volatile organic compounds from said wet scrubber to said anaerobic bioreactor.

8. The apparatus of claim 7 wherein said apparatus further comprises:

an agitated and closed buffer tank connected to said fluid transportation lines between said wet scrubber and said anaerobic bioreactor to allow a quick depletion of the oxygen contained in said liquid stream and a blending of said liquid stream loaded with the volatile solvents to provide a blended output stream thereby avoiding sharp peaks or drops in concentration of volatile organic solvents flowed to said anaerobic bioreactor;

a tank liquid level controller for controlling the amount of liquid in said tank and for controlling the flow of said liquid stream to said anaerobic bioreactor;

a temperature controller for measuring and controlling the temperature of said liquid stream;

a pH controller for measuring and controlling the pH of said liquid stream.

9. The apparatus of claim 8 wherein said agitated tank further comprises a nutrient addition port for adding nutrients and traces of heavy metals to the contents of said tank to enhance the operation of said anaerobic bioreactor.

10. The apparatus of claim 8 wherein said tank comprises a gas return line connected to the top of said tank and to said wet scrubber unit to return to said wet scrubber unit any volatile organic compounds and carbon dioxide which may have evaporated from the liquid contained in said tank.

11. The apparatus of claim 7 wherein said wet scrubber unit is a multiple stage wet scrubber comprising a plurality of serially interconnected sealed and columnar vessels.

12. The apparatus of claim 11 wherein said anaerobic bioreactor comprises:

an upstanding container having inlet means for receiving said liquid stream loaded with the volatile organic compounds and outlet means for discharging said liquid stream once treated in said bioreactor;

plate means in said container defining, above and below said plate means, upper and lower compartments;

a bed of methanogenic bacteria supported on said plate means in said upper compartment, said plate means having a plurality of aperture means there through to provide fluid flow communication between said upper and lower compartments;

blockage means in said upper compartment, associated with said aperture means, for preventing said liquid stream and said methanogenic bacteria from returning, through said apertures to said lower compartment;

means for releasing said methane-rich and combustible gas from said upper compartment of said container.

13. The apparatus of claim 12, wherein said lower compartment of said bioreactor comprises a bottom plate for supporting a further bed of methanogenic bacteria.

14. The apparatus of claim 7 further comprising a closed buffer tank connected to said fluid transportation lines between said wet scrubber and said anaerobic bioreactor to allow a quick depletion of the oxygen contained in said liquid stream, add nutrients and adjust the pH of the resulting liquid solution.

* * * * *

UNITED STATES PATENT AND TRADEMARK OFFICE
CERTIFICATE OF CORRECTION

PATENT NO. : 5,681,470
DATED : October 28, 1997
INVENTOR(S) : BECHARA SAFI

It is certified that error appears in the above-indentified patent and that said Letters Patent is hereby corrected as shown below:

Claim 4, col. 9, line 12, delete "deleting" and substitute therefor -- depleting --; Claim 7, col. 9, line 37, after "of" delete "a".

Signed and Sealed this

Seventeenth Day of February, 1998

Attest:

BRUCE LEHMAN

Attesting Officer        Commissioner of Patents and Trademarks

UNITED STATES PATENT AND TRADEMARK OFFICE
Certificate

Patent No. 5,681,470                                                          Patented: October 28, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bechara Safi, Ville-St-Laurent, Canada; and Catherine Mulligan, Montreal, Canada.

Signed and Sealed this Thirtieth Day of May 2006.

DUANE S. SMITH
*Supervisory Patent Examiner*
Art Unit 1724